(12) United States Patent
Fries et al.

(10) Patent No.: US 7,101,999 B2
(45) Date of Patent: Sep. 5, 2006

(54) OXAZINE DERIVATIVES

(75) Inventors: Joachim Fries, Tornesch (DE); Eloisa Lopez-Calle, Hamburg (DE); Karl-Heinz Drexhage, Siegen (DE)

(73) Assignee: Evotec AG, Hamburg (DE)

( * ) Notice: Subject to any disclaimer, the term of this patent is extended or adjusted under 35 U.S.C. 154(b) by 311 days.

(21) Appl. No.: 10/363,813

(22) PCT Filed: Sep. 5, 2001

(86) PCT No.: PCT/EP01/10236

§ 371 (c)(1),
(2), (4) Date: Jul. 14, 2003

(87) PCT Pub. No.: WO02/20670

PCT Pub. Date: Mar. 14, 2002

(65) Prior Publication Data

US 2004/0029837 A1    Feb. 12, 2004

(30) Foreign Application Priority Data

Sep. 6, 2000  (EP) ................... 00119292
Dec. 8, 2000  (EP) ................... 00127005

(51) Int. Cl.
*C07D 265/38*  (2006.01)
*G01N 33/532*  (2006.01)
*G01N 33/533*  (2006.01)
*G01N 33/53*   (2006.01)
*C07K 1/10*    (2006.01)

(52) U.S. Cl. ............... 544/99; 436/544; 436/546; 435/7.5; 530/391.3

(58) Field of Classification Search ............ 544/103, 544/99; 436/172, 544, 546, 824; 435/6, 435/7.1, 7.5; 530/413, 391.3
See application file for complete search history.

(56) References Cited

U.S. PATENT DOCUMENTS

| 1,488,609 | A | * | 4/1924 | Hoechst ............ 237/12.3 A |
| 4,714,763 | A | | 12/1987 | Theodoropulos |
| 4,780,535 | A | | 10/1988 | Theodoropulos |
| 5,532,171 | A | | 7/1996 | Motsenbocker |
| 5,656,759 | A | | 8/1997 | Ito et al. |
| 5,739,318 | A | | 4/1998 | Frantzen et al. |
| 5,792,389 | A | | 8/1998 | Hammond et al. |
| 5,917,035 | A | | 6/1999 | Birri et al. |
| 6,140,500 | A | | 10/2000 | Yan et al. |
| 6,166,202 | A | * | 12/2000 | Simmonds et al. .......... 544/99 |
| 6,908,769 | B1 | * | 6/2005 | Belik et al. ............ 436/172 |
| 2003/0224421 | A1 | * | 12/2003 | Herrmann et al. ........... 435/6 |

FOREIGN PATENT DOCUMENTS

| DE | 2411761 A1 | 10/1975 |
| DE | 287 040 A5 | 2/1991 |
| EP | 0 323 152 A2 | 7/1989 |
| EP | 0 603 129 B1 | 6/1994 |
| EP | 0 747 447 A2 | 12/1996 |
| GB | 1 488 609 | 10/1977 |
| WO | WO 90 03383 A1 | 4/1990 |
| WO | WO 92/08722 | * 5/1992 |
| WO | WO 97/29154 A1 | 8/1997 |
| WO | WO 99/07793 A1 | 2/1999 |
| WO | WO 01 42505 A2 | 6/2001 |

OTHER PUBLICATIONS

Frantzen et al. Labeling agents comprising boronic acid conjugates, their preparation and use in blood analysis. WO 9208722. CAPLUS search, document No. 118:61528, copied pp. 1-3.*

* cited by examiner

*Primary Examiner*—Mary E. Ceperley
*Assistant Examiner*—Shafiqul Haq
(74) *Attorney, Agent, or Firm*—Caesar, Rivise, Bernstein, Cohen & Pokotilow, Ltd.

(57) ABSTRACT

The invention relates to oxazine derivatives by means of which a broad spectrum of material to be examined can be marked and identified using fluorescence techniques.

8 Claims, No Drawings

OXAZINE DERIVATIVES

BACKGROUND OF THE INVENTION

The present invention relates to oxazine derivatives, methods for their production and their application as fluorescent dyes for labelling biological and non-biological materials in the red spectral range.

Oxazine-based dyes are widely used. They are frequently found in the textile industry for dyeing materials of various kinds. Thus, EP-B-0 603 129 describes oxazine dyes which each have exo-amino groups at the benzene rings which can be substituted. The barely soluble salts of these basic oxazine dyes are suitable for dyeing or printing natural fibres and completely synthetic fibres.

U.S. Pat. No. 5,656,759 discloses a cationic oxazine dye which also has two exo-amino groups which can be substituted. The oxazine dyes which can be made hydrophobic by substitution of inorganic anions are especially used in the ink layer of an ink ribbon for thermal transfer printing.

EP-A-0 747 447 discloses oxazine dyes used as fluorescence markers in connection with biological molecules. The absorption range of these conjugate forms is situated at 645–700 nm and corresponds to the red spectral range. The linkable oxazine derivatives are at least tetracyclic systems in which at least one of the two exocyclic nitrogens is integrated in the ring structure. As a result of the complex polycyclic basic structure, however, the expenditure for synthesising these dyes is very high.

Especially for high-throughput screening using confocal fluorescence spectroscopy there is a need for dyes which have a high fluorescence quantum yield, high solubility in water, high solubility in organic solvents, high chemical stability, high photostability and the capacity to bind to biological and non-biological materials or molecules.

As a result of the cheap access to red-emitting laser light sources and the low background fluorescence (autofluorescence) of biological material excited in the red compared with the energy-richer exciting wavelengths, the use of fluorescence dyes excitable in the red, including among others the oxazine dyes, is acquiring increasing importance.

As a result of conventional labelling methods, especially protein labelling methods, for example, using fluorescent detection markers, multiple reactive groups of these molecules are being targeted so that the labelling reaction results in a statistical labelling i.e., some proteins possess no labels, others possess one, two or more. In highly sensitive analytical techniques the heterogeneous analyte mixture leads to undesirable heterogeneous signal distributions which falsify the measurement results or make them completely unusable. In addition, as a result of interaction between the individual labellings in multiply labelled proteins, for example, there is a weakening of the signal.

The object of the present invention is to provide fluorescent dyes which avoid the aforesaid disadvantages of known fluorescent dyes and exhibit said positive properties. It is a further object of the invention to provide methods for producing these fluorescent dyes and a method for labelling material or molecules using these dyes. The object especially consists in providing red-excitable fluorescent dyes which are highly soluble in water, wherein the photochemical properties are retained. Furthermore, the dye should be activated in a fashion such that it is made capable of linking to biological and non-biological materials or molecules without there being any negative interaction with the materials or molecules to be labelled.

SUMMARY OF THE INVENTION

The invention achieves the aforementioned objects by providing oxazine derivatives having the general formula I

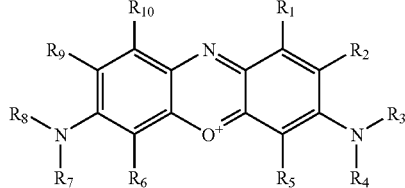

wherein
(a) the radicals $R_1$, $R_2$, $R_3$, $R_4$, $R_5$, $R_6$, $R_7$, $R_8$, $R_9$ and $R_{10}$ independently of one another denote hydrogen, alkyl, cycloalkyl, alkenyl, alkenoxy, aryl, aryldiazo, alkylaryl, arylalkoxyl, alkoxy, alkoxycarbonyl, hydroxy, halogen, cyano, carbonyl, acyl, acyloxy, carboxyl, carbonamide, halogen carbonamide, sulfonyl, sulfonyl halide, acid ester, acid anhydride, acid halide, imide, imidyl ester, isothiocyanate, phosphoramidite, azide, dithionicotine derivative or amine and are substituted if necessary,
(b) $R_1$ with $R_2$ and/or $R_9$ with $R_{10}$ can form a saturated or unsaturated C3 or C4 bridge which is/are substituted if necessary;
(c) the substituents independently of one another can denote alkyl, cycloalkyl, alkenyl, alkenoxy, aryl, aryldiazo, alkylaryl, arylalkoxyl, alkoxy, alkoxycarbonyl, hydroxy, halogen, cyano, carbonyl, acyl, acyloxy, carboxyl, carbonamide, halogen carbonamide, sulfonyl, sulfonyl halide, acid ester, acid anhydride, acid halide, imide, imidyl ester, isothiocyanate, phosphoramidite, azide, dithionicotine derivative or amine; and
(d) at least one of the radicals $R_1$, $R_2$, $R_3$, $R_4$, $R_5$, $R_6$, $R_7$, $R_8$, $R_9$ and $R_{10}$ comprises at least one reactive group for the binding to a material to be investigated or additionally has at least one reactive group, or a salt thereof.

The invention further provides a method for producing such oxazine derivatives, and a method for labelling comprising the use of such oxazine derivatives.

DETAILED DESCRIPTION OF THE INVENTION

In the sense according to the invention the radicals $R_1$ to $R_{10}$ can comprise the reactive group i.e., for example, represent and/or contain this. For example, a substituent can represent the reactive group. In addition, the oxazine derivative can possess a reactive group if the radicals comprise no reactive group. This reactive group can, for example, be bound to the non-reactive substituent.

The oxazine derivatives according to the invention can be present as tri- or tetra-pentacylic. In a preferred embodiment $R_1$ with $R_2$ and/or $R_9$ with $R_{10}$ forms a saturated or unsaturated C4 bridge. Especially $R_1$ with $R_2$ or $R_9$ with $R_{10}$ forms a saturated or unsaturated C4 bridge whereby a further six-membered ring appears at the tricyclic ring which is substituted if necessary. Quite especially preferred $R_1$ with $R_2$ forms an unsaturated $C_4$ bridge.

The reactive group serves to activate the dye, i.e., provides a site which creates a bond to the material to be studied. Reactive groups in the sense of the invention comprise activatable and activated groups. The bond to the material to be studied can be of a covalent or non-covalent nature wherein however the covalent linkage is preferred. It is preferred that only one reactive group is present per dye molecule. The activation can take place by light for example (photo-activation).

The reactive group can be any group which is capable of binding to the material to be studied. If the material to be studied is a protein, for example, various groups are then available for the binding to the dye. These include for example, amine from lysine radicals or thiol from free cystine or cystein radicals. For the labelling of oligonucleotides with the oxazine derivatives according to the invention during the synthesis of the oligonucleotide it is preferable to use an oxazine derivative according to the invention with a phosphoramidite group as the reactive group. The particularly high base stability of these oxazine derivatives allows them to be used simply and quickly in such synthesis reactions.

An exemplary list of preferred reactive groups comprises groups such as an acid ester, acid anhydride, acid halide, imide, imidyl ester, carboxyl, carbonamide, halogen carbonamide, sulfonyl halide, isothiocyanate, phosphoramidite, amine, aryldiazo, azide, aryldiazo, aldehyde, ketone or dithionicotine derivative.

Especially preferred reactive groups are an acid ester, acid anhydride, acid halide, imide, imidyl ester, carboxyl, carbonamide, halogen carbonamide, sulfonyl halide, isothiocyanate, phosphoramidite, amine, azide, aryldiazo, or dithionicotine derivative.

Quite especially preferred reactive groups are an N-succinimidyl ester which is substituted if necessary, maleimide, carboxyl, halogen acetamide, isothiocyanate, phosphoramidite, aryldiazo, azide, sulfonyl chloride, sulfo-tetrafluorophenol ester or primary or secondary amine.

For the case where the N-succinimidyl ester is substituted, a preferred substituent is the sulfonic acid group.

It has been found according to the invention that the oxazine derivatives can also contain a linker compound this linker compound is inserted between the reactive group and a non-bridge-forming radical $R_1$, $R_2$, $R_3$, $R_4$, $R_5$, $R_6$, $R_7$, $R_8$, $R_9$ or $R_{10}$. Preferably a reactive group of a non-bridge-forming radical combines with the linker compound. Preferably at least one reactive group is still bound to the linker compound after the combining. The linker compounds are introduced if there is a need to modify the reactive group in a simple fashion, i.e. to change the functionality. For example, the carbonic acid or the N-succinimidyl ester can be converted into an amine by means of a linker compound. On the other hand, the linker compounds make it possible to vary the distance between the dye and the material to be studied. The solubility of the oxazine derivatives can be simply matched to the respective solvents by means of linker compounds.

Suitable linker compounds include, for example, polyoxyalkyl units, aliphatic, cycloaliphatic or aromatic units. They can be branched or non-branched and can contain unsaturated units and hetero-atoms, e.g. nitrogen, if necessary.

Said polyoxyalkyl units are polymeric or oligomeric organic radicals which are interlinked via oxygen bridges. They include, for example polyether, polyols, soluble carbohydrates, derivatives thereof or water-soluble polymers.

As an example, linker compounds can be represented as follows (Y denotes "reactive group" in the following examples):

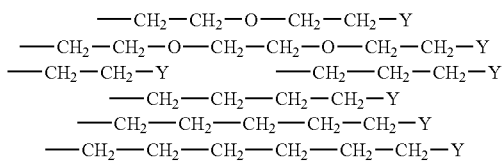

$$—[(CH_2)_n—O]_m—(CH_2)_r—Y$$

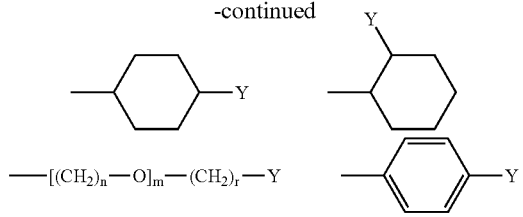

(as well as ortho- and meta-substitution)

The radicals and substituents alkyl, cycloalkyl, alkenyl, alkenoxy, alkylaryl, arylalkoxy, alkoxy, halogen carbonamide and alkoxycarbonyl generally have 1 to 10, preferably 1 to 7 carbon atoms and can be straight-chain or branched. One to four carbon atoms are especially preferred. In the case of aryl, these are preferably benzene rings.

Preferred are $R_3$, $R_4$, $R_7$ and $R_8$ alkyl radicals which are substituted if necessary and comprise the reactive groups. Other non-electron-attracting radicals are also preferred in various embodiments. These derivatives have an especially high fluorescence quantum yield.

Possible halogens are fluorine, chlorine, bromine or iodine.

Any anion suitable for charge neutralisation and compatible with the cationic basic structure which does not lower the solubility of the total compound in water or the solubility in other solvents such as DMSO, DMF or alcohols, can be used as the counterion. Preferred are halide ions, $BF_4^-$ or tetraphenyl borate. Especially preferred are chloride or bromide ions or tetraphenyl borate.

Especially preferred oxazine derivatives are special embodiments which are reproduced by the formulae II to V and VIII–IX:

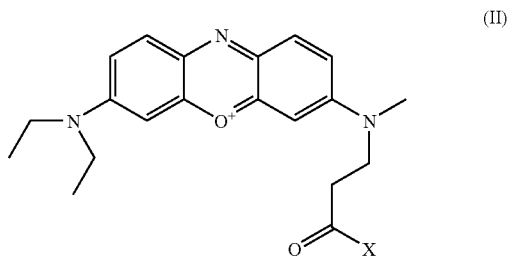

(II)

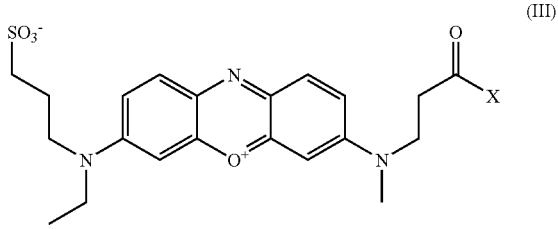

(III)

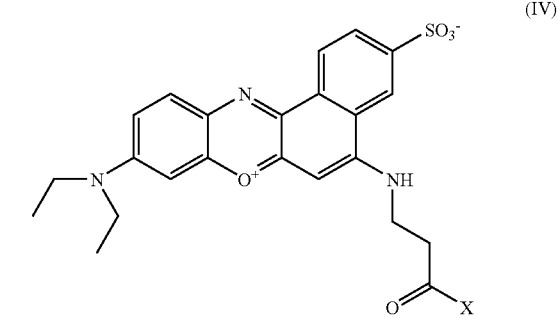

(IV)

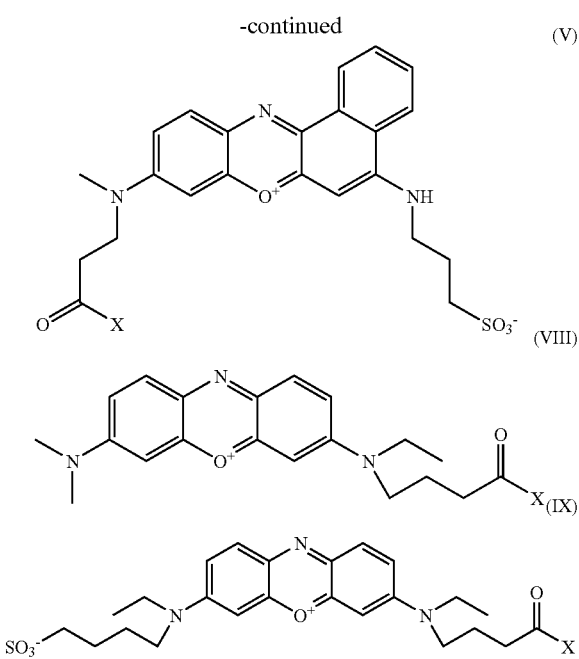

wherein X denotes OH, phosphoramidite or an N-succinidyl ester group which is substituted if necessary, wherein salts thereof are also included.

The advantages of oxazine dyes according to the invention compared with the UV dyes known so far such as coumarins or dyes excited by blue or green light such as fluoresceins and rhodamines, are as follows:
- high reactivity towards amines so that a large range of substances to be studied can be covalently labelled in a simple fashion;
- high solubility in water which leads to minimal absorption and minimal non-specific binding;
- high solubility in organic solvents such as, for example, DMSO, DMF or alcohols;
- excitation at 630 to 650 nm by means of cheap laser diodes or He—Ne lasers;
- emission with a maximum in the 670 nm range where normal filter arrangements can be used;
- high fluorescence quantum yield which produces clear and distinct fluorescence signals;
- solvent stability and pH stability (pH 1–10), so that they are suitable for very many applications;
- neutral overall charge which has the result that there is no electrostatic influence on the labelled molecule;
- chemical stability and thus extremely suitable for organic chemistry (solution and solid phase); and
- NIR excitability which leads to very low background fluorescence (autofluorescence) of the material to be studied.

The high symmetry of the oxazine derivatives according to the invention, especially derivatives II, III, IV and V brings about an especially high fluorescence quantum yield, high light absorption and sharp absorption bands.

A further decisive advantage of the dyes according to the invention will be shown using the following example of protein labelling. By means of conventional labelling methods, especially protein labelling methods, such as the reaction of an activated carbonic acid with lys radicals of the protein or of maleimides with free thiol groups of the protein, increasingly more of these protein groups are targeted so that a statistical distribution of the labelling on the protein is brought about by the labelling reaction, i.e., some protein molecules possess none, others have one, two, three or more labellings. For example, in high-sensitivity fluorescence techniques such as FCS (Fluorescence Correlation Spectroscopy) and FIDA (Fluorescence Intensity Distribution Analysis), this heterogeneous analyte mixture also leads to heterogeneous signal distributions which make it difficult to evaluate the data. In addition, in proteins carrying two, three or more labels, this results in dye-dye interactions which drastically weaken the fluorescence signal.

With the oxazine derivatives according to the invention however, it is possible to provide a singly labelled material to be studied for the analysis. It is thereby ensured that no heterogeneous signal distributions and dye-dye interactions occur. This leads to an appreciable improvement in the measurement results.

In principle, any measurable detection marker, for example, radioactive detection markers etc. can be used. Preferably used are dye markers, especially fluorescence markers. Quite especially preferably used are the oxazine derivatives according to the invention.

Instead of singly labelled fractions of the material to be studied, it may also be preferable, for example, to isolate doubly, triply, etc. labelled fractions.

The oxazine derivatives according to the invention can also have at least one affinity marker which allows simple purification by affinity chromatography. The affinity marker can, for example, be bound to the linker compound.

In a preferred embodiment the oxazine derivatives have only one affinity marker. In principle, it is possible to use any affinity marker which is suitable for performing a clean separation in the following affinity chromatography. As examples, affinity markers such as biotin, hexa-his or hapten may be mentioned at this point.

A method for targeted labelling of material to be studied using affinity-labelled oxazine derivatives can be implemented as follows:
a) Preparation of a sample comprising a material to be studied;
b) Reaction of the material to be studied with an oxazine derivative containing an affinity marker described above, wherein a mixture of labelled material to be studied is formed, labelled with none, one or several oxazine derivatives; and
c) Separation of the material to be studied into non-labelled, singly or multiply labelled fractions by affinity chromatography.

The method for targeted labelling of material to be studied using affinity-labelled detection markers can be implemented as follows:
a) Preparation of a sample comprising a material to be studied;
b) Reaction of the material to be studied with a detection marker containing an affinity marker described above, wherein a mixture of labelled material to be studied is formed, labelled with none, one or several oxazine derivatives; and
c) Separation of the material to be studied into non-labelled, singly or multiply labelled fractions by affinity chromatography.

Such an affinity purification using the oxazine derivatives according to the invention with the biotin/avidine system (affinity marker/carrier material) is presented in the following as an example.

By using the affinity-labelled dye reactive molecule according to the invention, which is presented below, the disadvantage of the known labelling techniques described above can be avoided. Here the biotin unit represents any affinity marker and the oxazine derivative III represents any dye marker, especially a dye according to the invention and the N-succinimidyl ester represents any reactive group. Such a molecule reacts analogously to the conventional labelling method with the protein which results in a heterogeneous mixture as described above. By means of a following affinity purification on a suitable carrier material (monomeric avidine in this case), unlabelled proteins are removed from the sample. Singly labelled proteins can be eluted by subsequent careful elution while doubly and higher-labelled proteins remain bound as a result of the cooperatively intensified binding to the carrier material. A homogeneous analyte with exactly one oxazine derivative according to the invention per protein molecule can thus be obtained.

necessary grafted with N,N'-bis-acryloylethylene diamine and polymer-coated glass particles. The biological microparticles are preferably vesicular particles or virus-like particles.

The biological material can, for example, be nucleotides, oligonucleotides, sugar, lipids, membranes, cells, cell constituents, DNA, RNA, peptides, proteins, antibodies, haptens or antigens.

Materials to be studied, especially biological material, can be labelled both in the liquid phase and combined with solid phases. In this case, both activated and activatable oxazine derivatives can be used. For example, the activation of

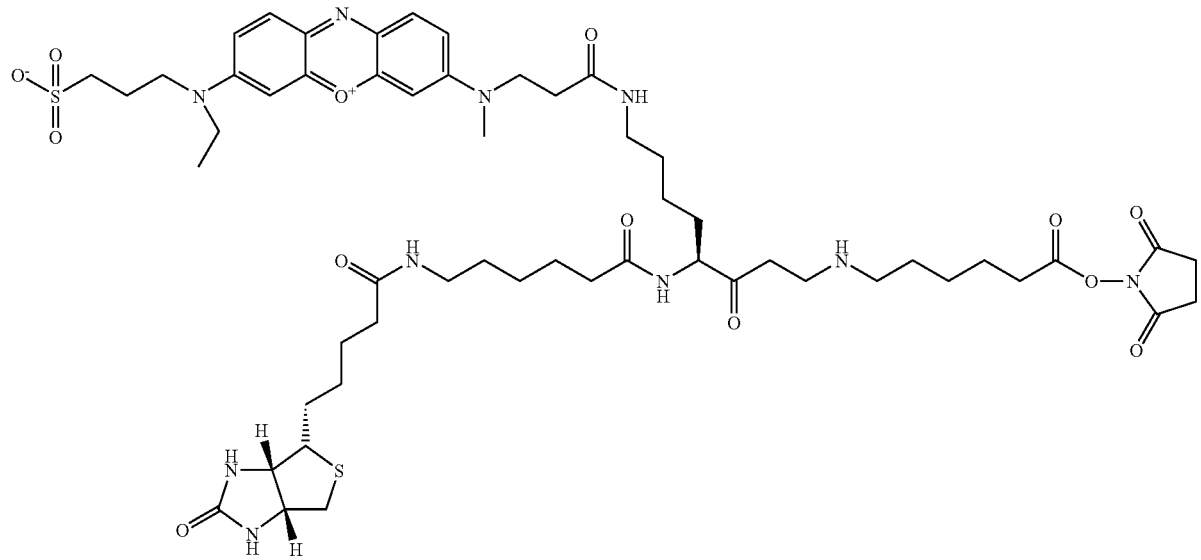

The material to be studied can be covalently or non-covalently bound to the oxazine derivative, wherein it is preferably covalently bound however. The material to be studied is preferably a biological material, a chemical compound, especially a biologically active substance and/or a pharmaceutical active ingredient, a synthetic or biological microparticle or a combination thereof.

The chemical compounds can comprise all synthetic compounds which are present as a single molecule or aggregate, for example, as a small organic compound or as an oligomer or polymer. The chemical compounds preferably comprise biologically active substances and/or pharmaceutical active ingredients.

Synthetic micro-particles, i.e., especially soluble and suspendable carrier materials, denote any type of synthetic micro-particles which can be dissolved or suspended in a liquid, especially an aqueous solution. The diameters d of the micro-particles are equal to or less than 1 µm, they preferably lie in the range 1 nm$\leq$d$\leq$1 µm, especially preferably in the range 10 nm$\leq$d$\leq$500 nm, quite especially preferably in the range 50 nm$\leq$d$\leq$300 nm. Examples of synthetic micro-particles comprise those of organic polymers. For example, dendrimer-based polymers, preferably dendrimer-based polyethylene glycol can be used. However, it is possible to use all synthetic micro-particles which are soluble or suspendable under the experimental conditions, especially glass particles having defined pore size, cellulose, silica gel and other types of polystyrene particles, the latter if necessary cross-linked with divinyl benzene and/or grafted with polyethylene glycol and/or functionalised with amino, hydroxy, carboxyl or halogen. Further examples of possible synthetic micro-particles comprise grafted co-polymer, polyacrylamide, latex, dimethylacrylamide particles if activatable oxazine derivatives, e.g. carboxy derivatives takes place in situ using activating reagents, such as for example benzotriazol-1-yl-oxy-tris-pyrrolidino-phosphonium hexafluorophosphate (PyBOB). Such activation is preferably carried out in solid-phase reactions.

The present invention also relates to a kit for labelling a material to be studied as described above. In addition to the usual constituents, this kit comprises an oxazine derivative according to the general formula I. Usual constituents are, for example, buffer, analytical vessels and instructions for carrying out the investigations. In a preferred embodiment this kit contains an oxazine derivative having the formula II, III, IV, V, VIII or IX, especially in the form of an N-succinimidyl ester which can be substituted if necessary. Especially preferred are kits with oxazine derivatives having the formula II, III, IV or V.

The material to be studied is preferably a biological material, a chemical compound, especially a biologically active substance and/or a pharmaceutical active ingredient, a synthetic or biological micro-particle or a combination thereof. The individual materials have already been described above.

The oxazine derivatives according to the invention are exceptionally suitable for chemical or biotechnical investigations. These include: the identification and characterisation of biological material or chemical compounds, the search for biologically active substances and/or pharmaceutical active ingredients, the identification of analytes in diagnostic and/or therapeutic methods, genome analysis (e.g. SNP analyses) or the purification and concentration of substrates.

Said investigations are preferably carried out using laser light analysis and fluorescence detection. The methods of measurement used in this case include almost all methods with which oxazine derivatives can be measured. These methods include spectrometry, multi-photon excitation, especially two-photon excitation, laser scanning microscopy, near-field spectroscopy, photon distribution analyses, especially FIDA and 2-D-FIDA, fluorescence lifetime analysis and fluorescence polarisation analysis. Quite especially preferably the measurements are carried out using a confocal microscope or other confocal optics.

The data is finally evaluated preferably by autocorrelation analysis and/or cross correlation analysis.

In 2-D-FIDA and cross-correlation analysis a measurement volume of a sample is irradiated simultaneously at two wavelengths and the information is obtained by means of a time coincidence analysis of two dye species, such as the oxazine derivatives according to the invention combined with green-excitable fluorescent dyes.

Similarly, the use in fluorescence resonance energy transfer experiments (FRET) is of great benefit wherein the oxazine derivatives according to the invention are used with a series of known xanthenes as a pair for energy transfer. The oxazine derivatives according to the invention can also be used very effectively in FISH (fluorescence in-situ hybridization) or PCR methods (polymerase chain reaction).

The oxazine dyes according to the invention are easily accessible synthetically, which differs from the compounds of the prior art which are substantially more difficult to produce. The dyes according to the invention, especially the derivatives II, III, IV or V, all have a very compact molecular structure so that the interaction with the material to be studied is estimated to be extremely small. Especially the biological properties of biological material are not modified. The generally neutral overall charge minimises the electrostatic interaction between the dye and the labelled component. The fluorescent dyes according to the invention have a high reactivity towards the materials to be studied, especially amines, a high fluorescence quantum yield, a high solvent resistance and pH resistance, a high chemical stability and NIR excitability. The dyes according to the present invention are characterised by a low excitation energy and thus by low photo-destruction. The particular excitation and emission wavelengths of the dyes according to the invention allow commercially available filter systems to be used. Also advantageous is the low background fluorescence (autofluorescence) of chemical and biological material excited in the red compared with energy-richer excitation wavelengths. The dyes according to the invention can thus be used very effectively in the red spectral range. The high chemical stability is especially important under conditions of solid-phase synthesis. The dyes according to the invention show a low adsorption or non-specific binding tendency and are highly soluble in water. They can thus ideally be used for chemical and biotechnical investigations in aqueous solutions, DMSO, DMF or alcohols.

The oxazine derivatives according to the invention can be prepared for example in the following way:

A 3-amino phenol having the formula VI

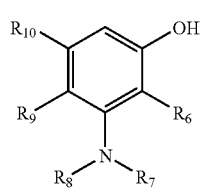

(VI)

is reacted with a nitrosophenyl compound having the formula VII

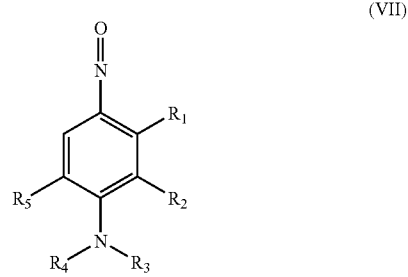

(VII)

in an acidic medium at moderate heat for period of 10 minutes to 5 hours. The radicals $R_1$ to $R_{10}$ have the meanings already specified above.

It has been found that the reaction is carried out at a temperature in the range of 50 to 70° C., preferably 55 to 65° C. For this purpose, the 3-amino phenol compound is dissolved in glacial acetic acid, for example, after which within a time interval in the range of 10 minutes to 5 hours the nitroso compound is added. After a deep-blue solution has formed, the reaction is generally ended. Purification is then carried out, normally by column chromatography.

Also included are the following synthesis possibilities wherein the initial compounds have the structures shown in the following:

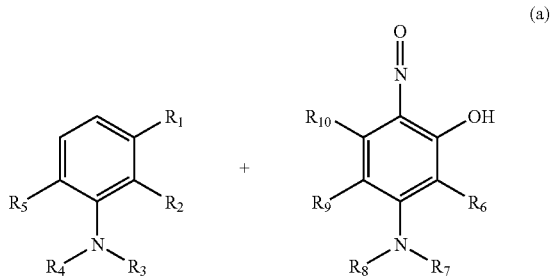

(a)

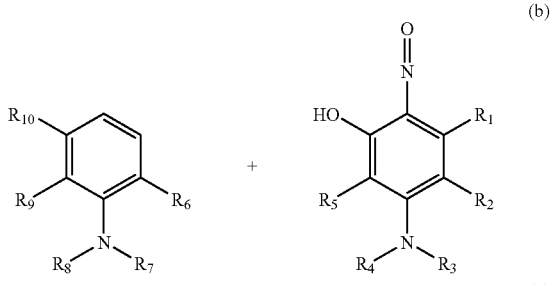

(b)

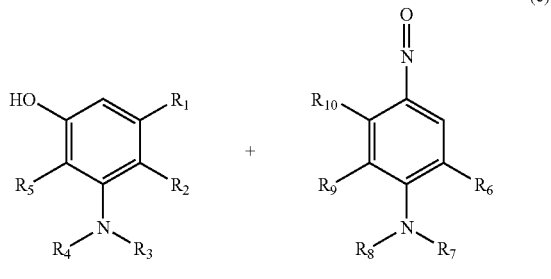

(c)

The following examples are used to explain the present invention.

EXAMPLES

Example 1

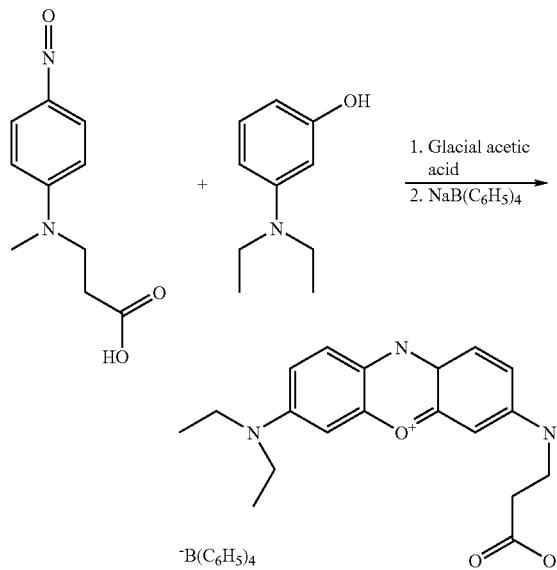

0.1 mol of 3-diethylaminophenol was dissolved in 20 ml of glacial acetic acid and heated to 60° C. Within 30 minutes 0.1 mol of 3-(N-methyl-N-(4-nitrosophenyl)-amino)propionic acid in 10 ml of glacial acetic acid was added to the solution. The now intensely blue solution was heated for 2 hours to reflux. After distilling off the glacial acetic acid, the residue was purified by column chromatography (eluent: ethanol/H$_2$O: 5:1; carrier: SiO$_2$). The bronze-coloured product [(2-carboxy-ethyl)-methylamino]-diethylaminophenoxazine-5-ylium was dissolved in water and precipitated using sodium tetraphenyl borate.

Example 2

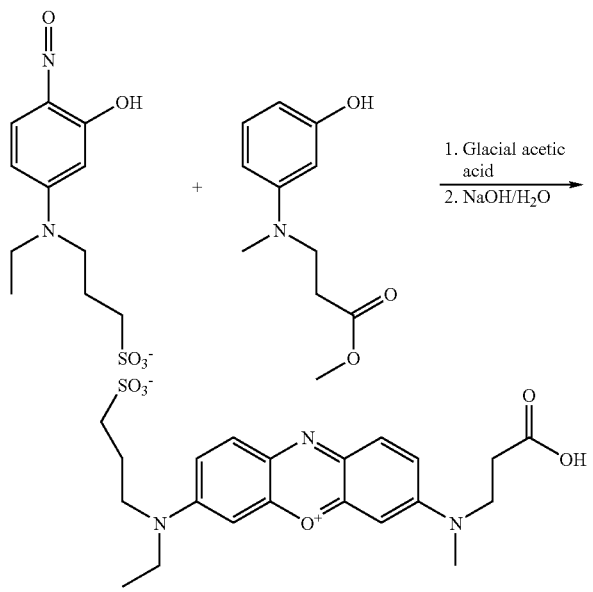

0.1 mol of N(-3-hydroxyphenyl)-N-methylamino-propionic acid methyl ester was dissolved in 50 ml of glacial acetic acid and heated to 60° C. Within 1 hour 0.1 mol of 3-(N-ethyl-N-(4-nitroso-3-hydroxyphenyl)-amino)propane sulfonic acid was added to the solution in portions. After a short time, a deep blue solution was formed. After a reaction time of three hours, the solution was concentrated and purified by column chromatography (eluent: ethanol; carrier: SiO$_2$). The product thus obtained was taken up in a 1N NaOH solution and treated for several hours in boiling heat. The solution was then evaporated to dryness and the raw product was separated by column chromatography (eluent: ethanol/H$_2$O: 10:1; carrier: SiO$_2$). After re-crystallisation from methanol, bronze-coloured crystals of [(2-carboxy-ethyl)-methyl-amino)]-[ethyl-(3-sulfo-propyl)-amino]-phenoxazine-5-ylium were obtained.

Example 3

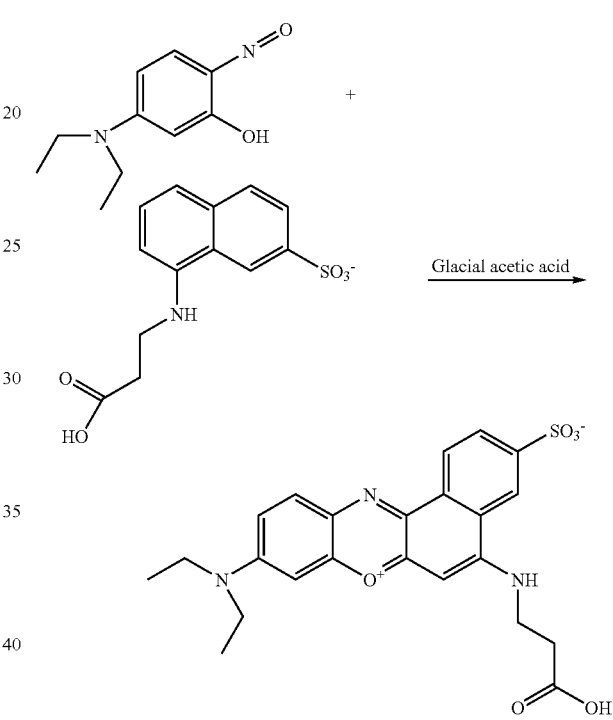

0.1 mol of 3-(7-sulfo-naphthylamino)-propionic acid and 0.1 mol of 5-(diethylamino)-2-nitroso-phenol were heated together in 20 ml of glacial acetic acid for 30 minutes to reflux. When the reaction solution was cooled, green crystals of (2-carboxy-ethylamino)-diethylamino-sulfobenzo[α]phenoxazine-7-ylium precipitated out. The solvent was removed and the raw product was purified by column chromatography (eluent: ethanol/water: 20:1; carrier: SiO$_2$). Re-crystallisation was carried out from glacial acetic acid.

Example 4

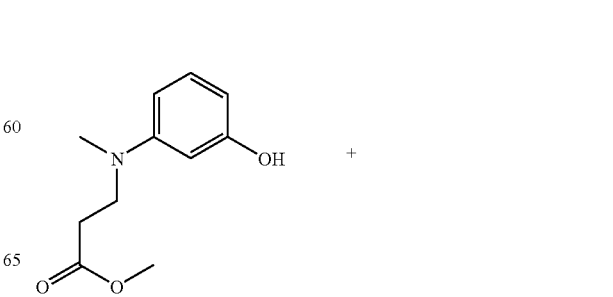

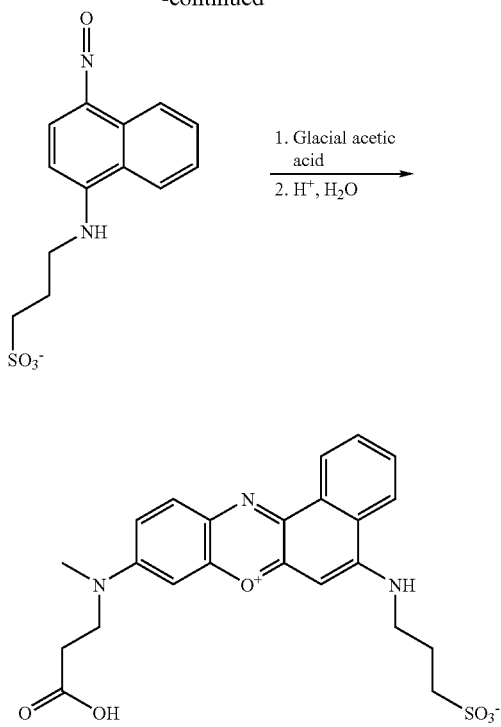

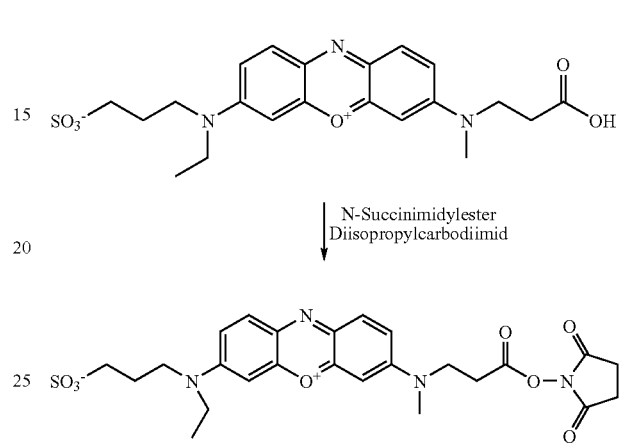

heated to reflux for 8 hours. The solvent mixture was then drawn off and the raw product was separated by column chromatography (eluent: ethanol/H$_2$O: 10/1; carrier SiO$_2$). After re-crystallisation from methanol, bronze-coloured crystals of (2-carboxy-ethylamino)-ethyl-(3-sulfo-propyl)-amino-benzo[α]phenoxazine-7-ylium were obtained.

Yield: 10%

Example 5

2 μmol of [(2-carboxy-ethyl)-methyl-amino]-[ethyl-(3-sulfo-propyl)-amino]-phenoxazine-5-ylium is dissolved in 200 μl of N,N-deimethyl formamide and a solution of 10 μmol of N-hydroxysuccinimide in 100 μl of N,N-dimethyl formamide and 2.4 μmol of diisopropylcarbodiimide added. This solution is shaken for 3 hours at room temperature and then concentrated to dryness. The conversion to [(2-carboxy-ethyl)-methyl-amino]-[ethyl-(3-sulfo-propyl)-amino]-phenoxazine-5-ylium succinimidyl ester is >90% and thus any further purification is unnecessary.

0.1 mol of N-(4-nitrosonaphthyl)-aminopropanesulfonic acid and 0.1 mol of N-(3-hydroxyphenyl)-N-methylaminopropionic acid methyl ester were heated together in 20 ml of glacial acetic acid for 30 minutes to reflux. After cooling the reaction solution, the solution was evaporated to dryness and the residue was re-crystallised from acetone. The product obtained was dissolved in a mixture of 10 ml of water and 10 ml of acetone, mixed with 1 ml of 1 N HCl solution and

Example 6

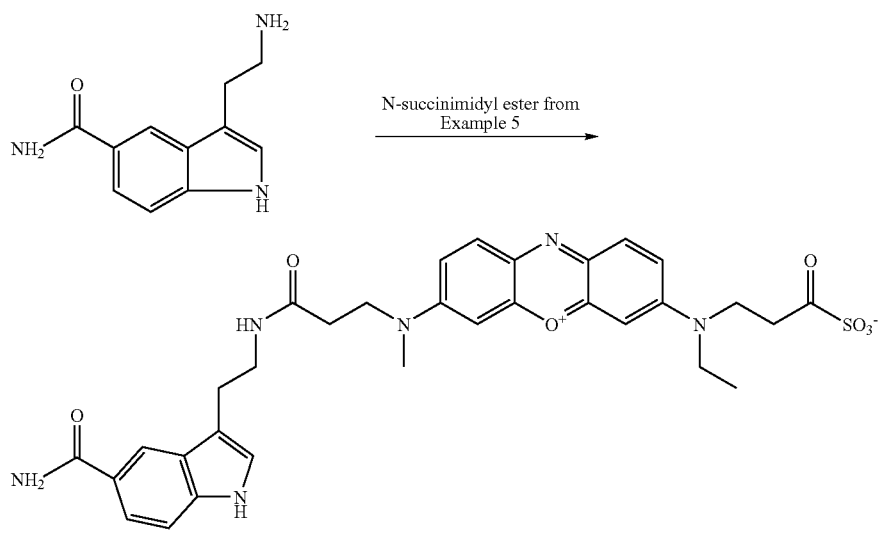

1 μmol of 5-carboxyamidotryptamine (5-CT) is dissolved in 50 μl of N,N-dimethyl formamide and added to a solution of 1.5 μmol of [(2-carboxy-ethyl)-methyl-amino]-[ethyl-(3-sulfo-propyl)-amino]-phenoxazine-5-ylium-succinimidyl ester in 200 μl of N,N-dimethyl formamide. To this solution is added 250 μl of 0.15 M pH 8.6 borate buffer and the reaction solution is shaken for 3 hours at room temperature. The solution is then concentrated to dryness and the raw product purified by column chromatography (eluent: methanol/water; gradient: 0% methanol to 100% methanol in 30 minutes; carrier: reversed phase C18).

Example 7

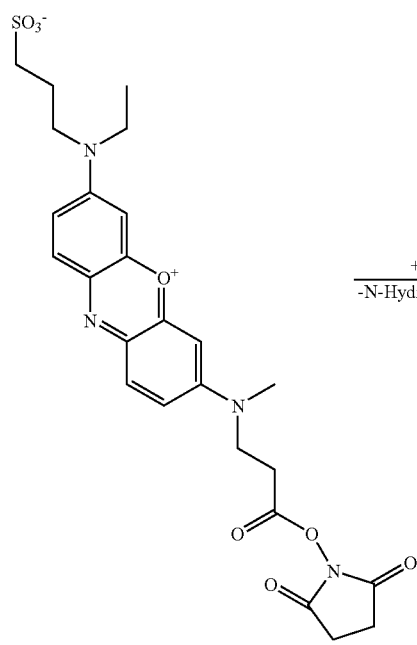

-continued 10 nmol of bovine IgG is dissolved in 150 μl of water. This solution is mixed with 15 μl of a 1 M pH 9.3 sodium carbonate solution and 331.4 μl of a 0.1 M pH 9.3 sodium carbonate solution as well as a solution of 50 nmol of [(2-carboxy-ethyl)-methyl-amino]-[ethyl-(3-sulfo-propyl)-amino]-phenoxazine-5-ylium-succinimidyl ester in 3.6 μl of N,N-dimethyl formamide and the reaction solution is shaken for 1 hour at room temperature. The reaction is then stopped by adding 50 μl of 1.5 M hydroxyamine solution. The raw product is then purified by exclusion chromatography (eluent: PBS pH 7.4).

Example 8

Introduction of a Linker in Oxazine Derivative (III)

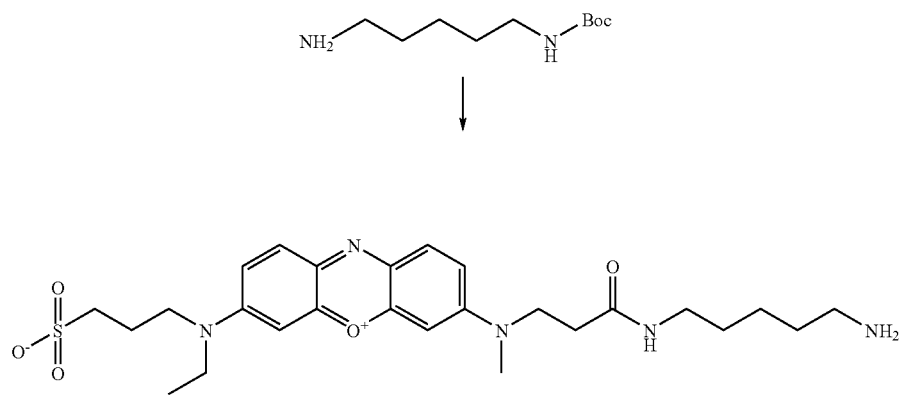

1. 2.0 eq Boc-cadaverine
   1.0 eq oxazine derivative (III)
   2.0 eq PyBOP
   5.0 eq DIPEA
2. 20% TFA in DCM 2 μmol of [(2-carboxy-ethyl)-methyl-amino]-[ethyl-(3-sulfo-propyl)-amino]-phenoxazine-5-ylium (oxazine derivative III) is dissolved in 200 μl of N,N-dimethyl formamide and a solution of 4 pmol of mono-t-butoxycarbonyl-1,5-diaminopentane (Boc-cadaverine) in 50 μl of N,N-dimethyl formamide, a solution of 4 μmol benzotriazol-1-yl-oxy-tris-pyrrolidino-phosphonium hexafluorophosphate (PyBOP) in 50 μl of N,N-dimethyl formamide and 10 μmol of N-ethyl-diisopropyl-amine (DIPEA) are added. This solution is shaken for 16 hours at room temperature and then concentrated to dryness. The residue is mixed with 300 μl of a solution of 20% trifluoroacetic acid (TFA) in dichloromethane (DCM) and shaken for 30 minutes at room temperature. The solution is concentrated to dryness and the raw product purified by column chromatography using HPLC.

Example 9

Introduction of a Linker in Oxazine Derivative (III)

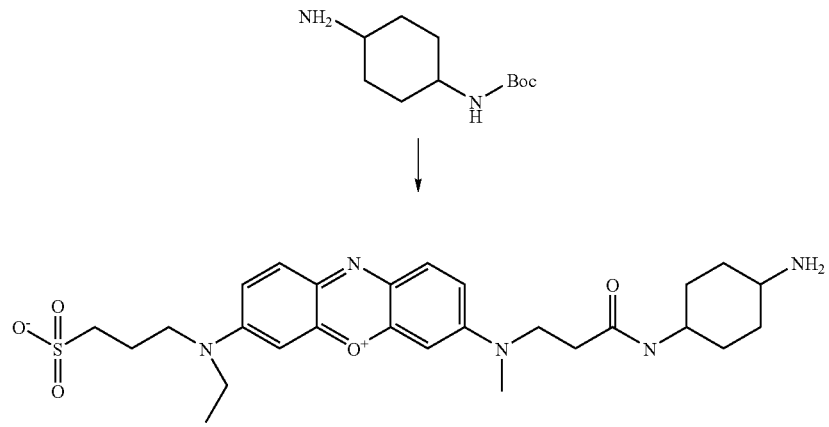

1. 2.0 eq Boc-CHA
   1.0 eq oxazine derivative (III)
   1.0 eq PyBOP
   4.0 eq DIPEA
2. 20% TFA in DCM 2 μmol of [(2-carboxy-ethyl)-methyl-amino]-[ethyl-(3-sulfo-propyl)-amino]-phenoxazine-5-ylium (oxazine derivative III) is dissolved in 200 μl of N,N-dimethyl formamide and a solution of 4 μmol of mono-t-butoxycarbonyl-trans-1,4-diaminocyclohexane (Boc-CHA) in 50 μl of N,N-dimethyl formamide, a solution of 2 μmol benzotriazol-1-yl-oxy-tris-pyrrolidino-phosphonium hexafluorophosphate (PyBOP) in 50 μl of N,N-dimethyl formamide and 8 μmol of N-ethyl-diisopropyl-amine (DIPEA) are added. This solution is shaken for 16 hours at room temperature and then concentrated to dryness. The residue is mixed with 300 μl of a solution of 20% trifluoroacetic acid (TFA) in dichloromethane (DCM) and shaken for 30 minutes at room temperature. The solution is concentrated to dryness and the raw product purified by column chromatography using HPLC.

Example 10

Affinity Marking 1 mmol of N-ε-(9-fluorenylmethoxycarbonyl)-aminohexanoic acid was dissolved in 1200 μl of dichloromethane and 300 μl of N,N-dimethyl formamide (DMA) and cooled to 0° C. 500 μl of N,N'-diisopropylcarbodiimide was dissolved in 80 μl of N,N-dimethyl formamide and added to the amino acid solution. The reaction solution was left to stand for 30 minutes at 0° C. and the dichloromethane was then removed in vacuum. The residue was taken up with 1000 μl of N,N-dimethyl formamide, wherein a clear solution was obtained. This solution was added to 100 μl of Wang resin in a 5 ml syringe with a frit. To the suspension was added 10 μmol of dimethylaminopyridine in 25 μl of N,N-dimethyl formamide and the mixture was left to stand overnight.

The resin was then washed six times with 2 ml of N,N-dimethyl formamide and three times with 2 ml of dichloromethane and six times with 2 ml of t-butylmethyl-ether, dried and weighed to determine the loading. The specific loading of the resin was 0.8 mmol/g resin. For further loading the 9-fluorenylmethoxycarbonyl protective group (FMOC) was initially separated by twofold treatment for 5 and 15 minutes respectively using a solution of 20% piperidine in N,N-dimethyl formamide. The resin was then washed six times with 2 ml of N,N-dimethyl formamide. 1 mmol of N-α-(9-fluorenylmethoxycarbonyl)-ε-(4-methyl-trityl)-L-lysine dissolved in 120 μl of N,N-dimethyl formamide as well as 1 mmol of 1-[bis(dimethylamino)methyli-umyl]-1H-1,2,3-triazolo[4,5-b]pyridine-3-oxide hexafluorophosphate dissolved in 120 μl of N,N-dimethyl formamide were added to the resin together with 2 mmol of N,N-diisopropylethylamine. The reaction solution was drawn off after 30 minutes and the loading process was repeated again under identical conditions.

After washing the resin six times each using 2 ml of N,N-dimethyl formamide, the 9-fluorenylmethoxycarbonyl protective group was separated by twofold treatment for 5 and 15 minutes respectively using a solution of 20% piperidine in N,N-dimethyl formamide. The resin was then again washed six times with 2 ml of N,N-dimethyl formamide. Then followed the reaction with 250 μl of biotinoyl-aminohexanoyl-N-hydroxy-succinimidyl ester in 300 μl of N,N-dimethyl formamide. After reacting for 10 hours, the reaction solution was drawn off, and the resin was washed six times with 2 ml of N,N-dimethyl formamide and three times with 2 ml of dichloromethane and six times with 2 ml of t-butylmethyl ether and dried.

For loading with the fluorescent dye, 10 µmol of the resin was removed and transferred to a 5 ml syringe. After the resin had been pre-soaked in 2 ml of dichloromethane, the 4-methyltrityl protective group (MTT) was separated by five three-minute treatments each with 2 ml of 30% hexafluorisopropanol (HFIP) in dichloromethane. The resin was then washed six times with 2 ml of dichloromethane and three times with 2 ml of N,N-dimethyl formamide. Then followed the reaction with 25 µmol of [(2-carboxy-ethyl)-methyl-amino]-ethyl-(3-sulfo-propyl)-amino]-phenoxine-5-ylium-succinimidyl ester in 300 µl of N,N-dimethyl formamide for three hours at room temperature. After the reaction had taken place, the resin was washed six times with 2 ml of N,N-dimethyl formamide, six times with 2 ml of dichloromethane, six times with 2 ml of methanol and six times with 2 ml of t-butylmethyl ether and dried. The product was now separated from the resin using a mixture of 95% trifluoroacetic acid (TFA), 2.5% water and 2.5% triisopropylsilane (TIS). After a reaction time of two hours, the solution was filtered off from the resin and concentrated in vacuum. The raw product left as residue was then taken up in methanol and purified by chromatography.

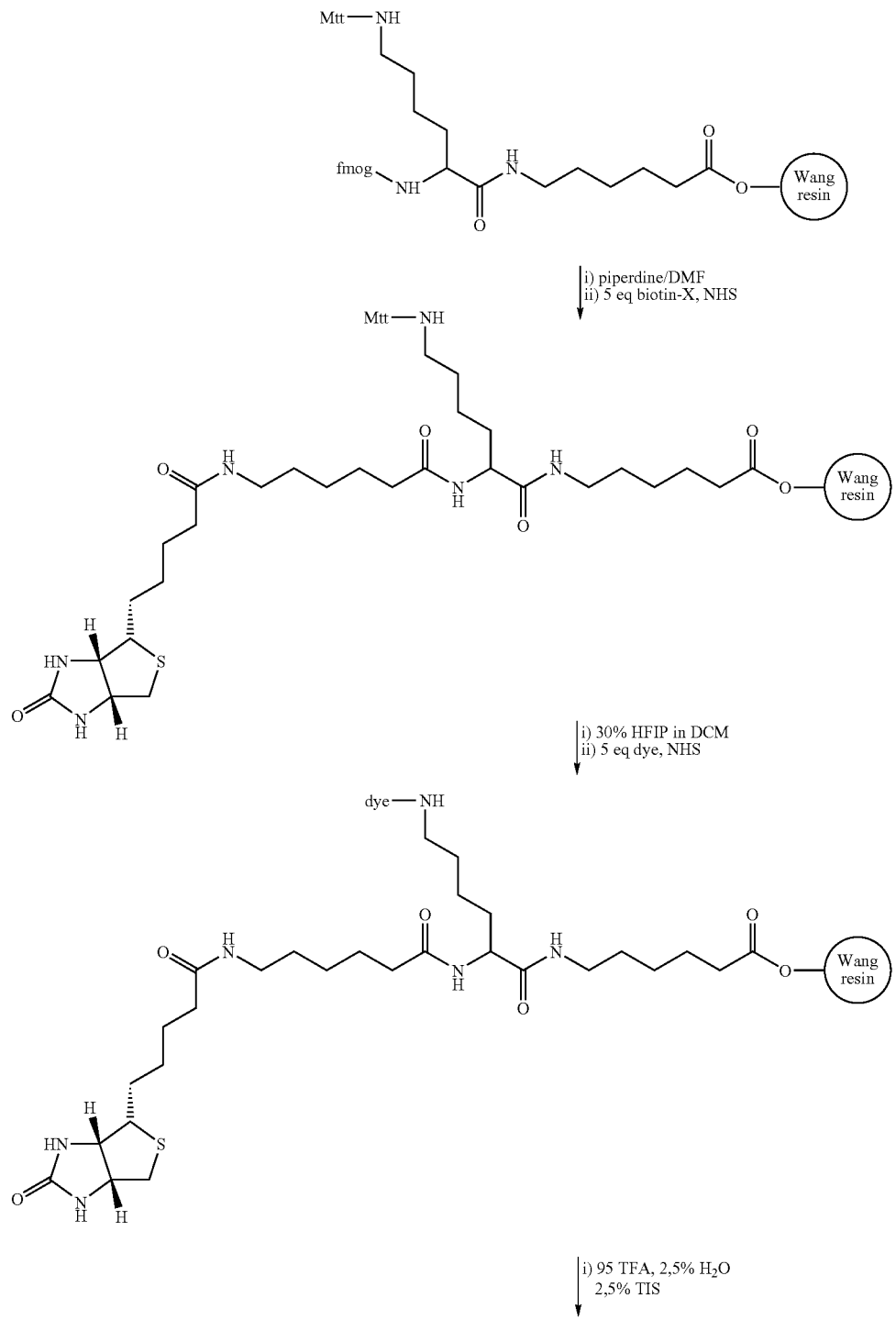

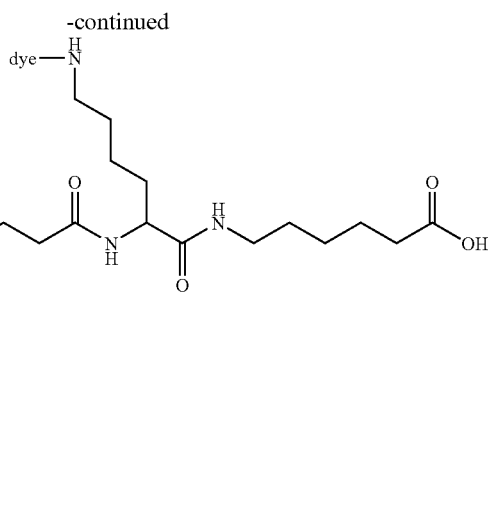

What is claimed is:

1. An oxazine derivative having the formula (IV)

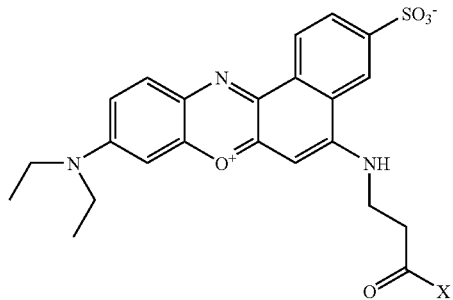

wherein X denotes OH, phosphoramidite or an optionally substituted N-succinimidyl ester group, or a salt thereof.

2. An oxazine derivative having the formula (V)

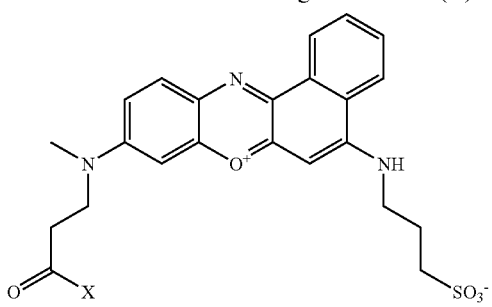

wherein X denotes OH, phosphoramidite or an optionally substituted N-succinimidyl ester group, or a salt thereof.

3. The oxazine derivative according claim 1, wherein the salt thereof contains a counterion selected from the group consisting of a halogen ion, a $BF_4^-$ ion or tetraphenyl borate.

4. The oxazine derivative according to claim 3, wherein the counterion is a chloride or bromide ion or tetraphenyl borate.

5. The oxazine derivative according claim 2, wherein the salt thereof contains a counterion selected from the group consisting of a halogen ion, a $BF_4^-$ ion or tetraphenyl borate.

6. The oxazine derivative according to claim 5, wherein the counterion is a chloride or bromide ion or tetraphenyl borate.

7. A kit for labelling a material to be studied, said kit comprising an oxazine derivative according to claim 1.

8. A kit for labelling a material to be studied, said kit comprising an oxazine derivative according to claim 2.

* * * * *